US005717062A

United States Patent [19]
Chorev et al.

[11] Patent Number: 5,717,062
[45] Date of Patent: Feb. 10, 1998

[54] CYCLIC ANALOGS OF PTH AND PTHRP

[75] Inventors: Michael Chorev, Brookline; Michael Rosenblatt, Newton Center, both of Mass.

[73] Assignee: Beth Israel Hospital Association, Boston, Mass.

[21] Appl. No.: 488,105

[22] Filed: Jun. 7, 1995

[51] Int. Cl.$^6$ .............................. A61K 38/00; C07K 5/00; C07K 7/00; C07K 16/00
[52] U.S. Cl. .................................................... 530/317
[58] Field of Search ............................................. 530/317

[56] References Cited

U.S. PATENT DOCUMENTS 4,968,669  11/1990  Rosenblatt ...................... 514/12

OTHER PUBLICATIONS

Fukuda et al.; EP-561412-A; New Parathyroid derivatives-Used for the treatment of osteoporosis hypoparathyroidism and hypertension Sep. 22, 1993 (Abstract).
Chorev et al.; Cyclic Parathyroid Hormone Related Protein Antagonists: Lysine 13 to Aspartic Acid 17 [i to (i+4)] Side Chain to side Chain Lactamization; Biochem.; 1991; 30;5968–5974.
Olstad et al.; Biochemistry; 1992; 205; 311–319.
Albert et al.; Patent 190 GB2269176-A; 1994.
Chorev et al., "Circular Dichroism (CD) Studies of Antagonists Dervived from Parathyroid Hormone–Related Protein", Int. J. Peptide Protein Res. 43:342–342, 1993.
Chorev et al., "Cyclic Parathyroid Hormone Related Protein Antagonists: Lysine 13 to Aspartic Acid 17 [i to (i + 4)] Side Chain to Side Chain Latamization", Biochemistry 30:5968–5974, 1991.

Neugebauer et al., "Structure and Protein Kinase C Stimulating Activities of Lactam Analogues of Human Parathyroid Hormone Fragment", Int. J. Peptide Protein Res. 43:555–562, 1994.

Broadus et al., "Parathyroid Hormone–related Protein", The Parathyroid, Chapter 17, pp. 259–294, 1994.

Dempster et al., "Anabolic Actions of Parathyroid Hormone on Bone", Endocrine Reviews, 14:690–709, 1993.

Hesch et al., "Increase of Vertebral Density by Combination Therapy with Pulsatile 1–38hPTH and Sequential Addition of Calcitonin Nasal Spray in Osteoporotic Patients", Calcif Tissue Int, 44:176–180, 1989.

Nissenson et al., "Structure and Function of the Receptor for Parathyroid Hormone and Parathyroid Hormone–Related Protein", Humana Press Inc., 3:193–202, 1993.

B. Lawrence Riggs, M.D., "Treatment of Osteoporosis with Sodium Fluoride or Parathyroid Hormone", The American Journal of Medicine, 91 (suppl 5B), 5B–37S–5B–41S, 1991.

Slovik et al., "Restoration of Spinal Bone in Osteoporotic Men by Treatment with Human Parathyroid Hormone (1–34) and 1,25–Dihydroxyvitamin D", Journal of Bone and Mineral Res., 1:377–381, 1986.

*Primary Examiner*—Cecilia J. Tsang
*Assistant Examiner*—Jennifer Harle
*Attorney, Agent, or Firm*—Fish & Richardson P.C.

[57] ABSTRACT

Cyclic analogs of PTH and PTHrP wherein a disulfide or amide bond links the side chains of residues $A_{13}$ and $A_{17}$, $A_{26}$ and $A_{30}$, or $A_{13}$ and $A_{17}$ and $A_{26}$ and $A_{30}$.

16 Claims, No Drawings

CYCLIC ANALOGS OF PTH AND PTHRP

BACKGROUND OF THE INVENTION

Parathyroid hormone ("PTH") is a polypeptide produced by the parathyroid glands. The mature circulating form of the hormone is comprised of 84 amino acid residues. Parathyroid hormone-related protein ("PTHrP") is a 139 to 173 amino acid-protein with N-terminal homology to PTH. PTHrP shares many of the biological effects of PTH including binding to a common PTH/PTHrP receptor. See Chipani, E., et al., Endocrinology, 1993 132, 2157–2165; Broadus, A. E., Steward, A. F., Parathyroid hormone-related protein: In: The Parathyroids, Bilezikian, J. P., et al., Eds, Raven Press, N.Y. 1994, 259–294. Many homologs of both PTH and PTHrP have been characterized. See Nissenson, R., et al., Structure & Function of the Receptor for Parathyroid Hormone and Parathyroid Hormone-Related Protein, 3 Receptor 193–202, 1993; and Burtis, W. J., 38(11) Clinical Chemistry 2171–2183 (1992).

PTH has been shown to effect a positive bone balance. See Dempster, D. W., et al., Endocrine Rev., 1993, 14, 690–709; and Riggs, L., Amer. J. Med., 1991, 91 (Suppl 5B), 37S–41S. The anabolic effect of intermittently administered PTH has been observed in osteoporotic men (Slovik, D. M., et al., J. Bone Miner. Res., 1986, 1, 377–381), women (Reeve, J., et al., Br. Med. J., 1990, 301, 314–318), and with concurrent antiresorptive therapy (Hesch, R-D., et al., Calcif Tissue Int, 1989, 176–180).

SUMMARY OF THE INVENTION

In one aspect, the invention relates to cyclic peptide analogs of PTH covered by the following generic formula:

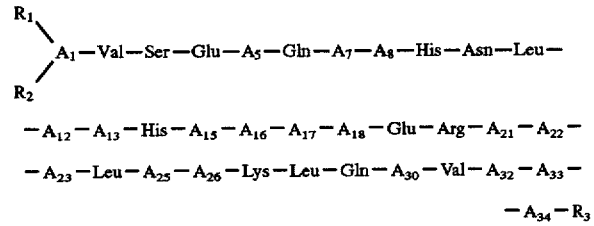

wherein:

$A_1$ is Ser or Ala;

$A_5$ is Ile or Met;

$A_7$ is Leu or Phe;

$A_8$ is Met, Nle, or Val;

$A_{12}$ is Gly, Glu, Aib, Ala, or D-Ala;

$A_{13}$ is the D- or L- isomer selected from the group consisting of Cys, Hcy, Lys, Orn, —NHCH(CH$_2$NH$_2$)CO—, —NHCH((CH$_2$)$_2$NH$_2$)CO—, Asp, Glu, —NHCH((CH$_2$)$_3$COOH)CO—, and —NHCH((CH$_2$)$_4$COOH)CO—;

$A_{15}$ is Leu, or Arg;

$A_{16}$ is Ser, His, Asn, or Ala;

$A_{17}$ is the D- or L- isomer selected from the group consisting of Ser, Thr, Cys, Hcy, Lys, Orn, —NHCH(CH$_2$NH$_2$)CO—, —NHCH((CH$_2$)$_2$NH$_2$)CO—, Asp, Glu, —NHCH((CH$_2$)$_3$COOH)CO—, and —NHCH((CH$_2$)$_4$COOH)CO—;

$A_{18}$ is Met, Leu, Nle, or Val;

$A_{21}$ is Met, Leu, Nle, Gln, or Val;

$A_{22}$ is Glu, Asp, or Gln;

$A_{23}$ is Trp, 1-Nal, or 2-Nal;

$A_{25}$ is Arg, or Gln;

$A_{26}$ is the D- or L- isomer selected from the group consisting of Met, Cys, Hcy, Lys, Orn, —NHCH(CH$_2$NH$_2$)CO—, —NHCH((CH$_2$)$_2$NH$_2$)CO—, Asp, Glu, —NHCH((CH$_2$)$_3$COOH)CO—, and —NHCH((CH$_2$)$_4$COOH)CO—;

$A_{30}$ is the D- or L- isomer selected from the group consisting of Cys, Hcy, Lys, Orn, —NH—CH(CH$_2$NH$_2$)CO—, —NHCH((CH$_2$)$_2$NH$_2$)CO—, Asp, Glu, —NHCH((CH$_2$)$_3$COOH)CO—, and —NHCH((CH$_2$)$_4$COOH)CO—;

$A_{32}$ is His or is deleted;

$A_{33}$ is Asn, Ser, or is deleted;

$A_{34}$ is Ala, Phe, p-X-Phe (where X is a halogen, CH$_3$, or OH), or is deleted;

each of $R_1$ and $R_2$ is, independently, H, $C_{1-12}$ alkyl, $C_{7-20}$ phenylalkyl, $C_{11-20}$ napthylalkyl, $C_{1-12}$ hydroxyalkyl, $C_{7-20}$ hydroxyphenyl, $C_{11-20}$ hydroxynapthylalkyl, or COE$_1$ where E$_1$ is $C_{1-12}$ alkyl, $C_{7-20}$ phenylalkyl, $C_{11-20}$ napthylalkyl, $C_{1-12}$ hydroxyalkyl, $C_{7-20}$ hydroxyphenylalkyl, or $C_{11-20}$ hydroxynapthylalkyl;

$R_3$ is OH, NH$_2$, $C_{1-12}$ alkoxy, or NH—Y—CH$_2$—Z where Y is a $C_{1-12}$ hydrocarbon moiety and Z is H, OH, CO$_2$H or CONH$_2$; or a pharmaceutically acceptable salt thereof; and a disulfide or amide bond links the side chains of residues $A_{13}$ and $A_{17}$, $A_{26}$ and $A_{30}$, or $A_{13}$ and $A_{17}$ and $A_{26}$ and $A_{30}$.

The following are examples of the cyclic peptides of this invention as covered by the above formula: c[Lys$^{13}$, Asp$^{17}$] hPTH(1-34)NH$_2$(SEQ ID NO:1); c[Lys$^{13}$, Asp$^{17}$]bPTH(1-34)NH$_2$(SEQ ID NO:2); c[Lys$^{13}$, Asp$^{17}$] rPTH(1-34)NH$_2$ (SEQ ID NO:3); c[Lys$^{13}$, Asp$^{17}$][Nle$^{8,18}$, Tyr$^{34}$]hPTH(1-34) NH$_2$(SEQ ID NO:4); c[Lys$^{13}$, Asp$^{17}$][Nle$^{8,18}$,Tyr$^{34}$Asp$^{17}$] [Nle$^{8,18}$, Tyr$^{34}$]bPTH(1-34)NH$_2$(SEQ ID NO:6); c[Lys$^{26}$, Asp$^{30}$]hPTH(1-34)NH$_2$(SEQ ID NO:7); c[Lys$^{26}$, Asp$^{30}$] bPTH(1-34)NH$_2$(SEQ ID NO:8); c[Lys$^{26}$, Asp$^{30}$]rPTH(1-34)NH$_2$(SEQ ID NO:9); c[Lys$^{26}$, Asp$^{30}$][Nle$^{8,18}$, Tyr$^{34}$] hPTH(1-34)NH$_2$(SEQ ID NO:10); c[Lys$^{26}$, Asp$^{30}$] [Nle$^{8,18}$, Tyr$^{34}$]bPTH(1-34)NH$_2$(SEQ ID NO:11); c[Lys$^{26}$, Asp$^{30}$] [Nle$^{8,18}$, Tyr$^{34}$] rPTH(1-34)NH$_2$(SEQ ID NO:12); c[Lys$^{13}$, Asp$^{17}$]c[Lys$^{26}$, Asp$^{30}$]hPTH(1-34)NH$_2$(SEQ ID NO:13); c[Lys$^{13}$, Asp$^{17}$]c[Lys$^{26}$, Asp$^{30}$]bPTH(1-34)NH$_2$(SEQ ID NO:14); c[Lys$^{13}$, Asp$^{17}$]c[Lys$^{26}$, Asp$^{30}$]rPTH(1-34)NH$_2$ (SEQ ID NO:15); c[Lys$^{13}$, Asp$^{17}$]c[Lys$^{26}$, Asp$^{30}$][Nle$^{8,18}$, Tyr$^{34}$] hPTH(1-34)NH$_2$(SEQ ID NO:16); c[Lys$^{13}$, Asp$^{17}$]c [Lys$^{26}$, Asp$^{30}$][Nle$^{8,18}$, Tyr$^{34}$]rPTH (1-34)NH$_2$(SEQ ID NO:17); or c[Lys$^{13}$, Asp$^{17}$] c[Lys$^{26}$, Asp$^{30}$][Nle$^{8,18}$, Tyr$^{34}$] bPTH(1-34)NH$_2$(SEQ ID NO:18); or a pharmaceutically acceptable salt thereof.

In another aspect, the invention relates to cyclic peptide analogs of PTHrP covered by the following generic formula:

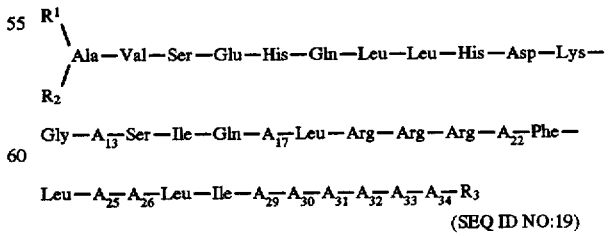

(SEQ ID NO:19)

wherein:

$A_{13}$ is the D- or L- isomer selected from the group consisting of Cys, Hcy, Lys, Orn, —NHCH(CH$_2$NH$_2$)

CO—, —NHCH((CH$_2$)$_2$NH$_2$)CO—, Asp, Glu, —NHCH((CH$_2$)$_3$COOH)CO—, and —NHCH((CH$_2$)$_4$COOH)CO—;

A$_{17}$ is the D- or L- isomer selected from the group consisting of Cys, Hcy, Lys, Orn, —NHCH(CH$_2$NH$_2$)CO—, —NHCH((CH$_2$)$_2$NH$_2$)CO—, Asp, Glu, —NHCH((CH$_2$)$_3$COOH)CO—, and —NHCH((CH$_2$)$_4$COOH)CO—;

A$_{22}$ is Phe or Ile;

A$_{25}$ is His or Gln;

A$_{26}$ is the D- or L- isomer selected from the group consisting of His, Asn, Cys, Hcy, Lys, Orn, —NHCH(CH$_2$NH$_2$)CO—, —NHCH((CH$_2$)$_2$NH$_2$)CO—, Asp, Glu, —NHCH((CH$_2$)$_3$COOH)CO—, and —NHCH((CH$_2$)$_4$COOH)CO—;

A$_{29}$ is Ala or Glu;

A$_{30}$ is the D- or L- isomer selected from the group consisting of Glu, Gly, Cys, Hcy, Lys, Orn, —NHCH(CH$_2$NH$_2$)CO—, —NHCH((CH$_2$)$_2$NH$_2$)CO—, Asp, Glu, —NHCH((CH$_2$)$_3$COOH)CO—, and —NHCH((CH$_2$)$_4$COOH)CO—;

A$_{31}$ is Ile or Val; and

A$_{32}$ is His, Asn, or is deleted;

A$_{33}$ is Thr or is deleted;

A$_{34}$ is Ala or is deleted;

each of R$_1$ and R$_2$ is, independently, H, C$_{1-12}$ alkyl, C$_{7-20}$ phenylalkyl, C$_{11-20}$ napthylalkyl, C$_{1-12}$ hydroxyalkyl, C$_{7-20}$ hydroxyphenyl, C$_{11-20}$ hydroxynapthylalkyl, or COE$_1$ where E$_1$ is C$_{1-12}$ alkyl, C$_{7-20}$ phenylalkyl, C$_{11-20}$ napthylalkyl, C$_{1-12}$ hydroxyalkyl, C$_{7-20}$ hydroxyphenylalkyl, or C$_{11-20}$ hydroxynapthylalkyl;

R$_3$ is OH, NH$_2$, C$_{1-12}$ alkoxy, or NH—Y—CH$_2$—Z where Y is a C$_{1-12}$ hydrocarbon moiety and Z is H, OH, CO$_2$H or CONH$_2$; or a pharmaceutically acceptable salt thereof; and a disulfide or amide bond links the side chains of residues A$_{13}$ and A$_{17}$, A$_{26}$ and A$_{30}$, or A$_{13}$ and A$_{17}$ and A$_{26}$ and A$_{30}$.

The following are examples of the cyclic peptide of this invention as covered by the above formula: c[Lys$^{13}$, Asp$^{17}$]hPTHrP(1-34)NH$_2$(SEQ ID NO:20); c[Lys$^{26}$, Asp$^{30}$]hPTHrP(1-34)NH$_2$(SEQ ID NO:21); or c[Lys$^{13}$, Asp$^{17}$]c[Lys$^{26}$, Asp$^{30}$]hPTHrP(1-34)NH$_2$(SEQ ID NO:22); or a pharmaceutically acceptable salt thereof.

With the exception of the N-terminal amino acid, all abbreviations (e.g. Ala or A$_1$) of amino acids in this disclosure stand for the structure of —NH—CH(R)—CO—, wherein R is a side chain of an amino acid (e.g., CH$_3$ for Ala). For the N-terminal amino acid, the abbreviation stands for the structure of =N—CH(R)—CO—, wherein R is a side chain determinant of an amino acid. 1-Nal, 2-Nal, Nle, Orn, Hcy and Aib are respective abbreviations of the following α-amino acids: 3-(1-naphthyl)alanine, 3-(2-naphthyl)alanine, norleucine, ornithine, homocysteine and α-aminoisobutyric acid, respectively. Also, in the above formula, hydroxyalkyl, hydroxyacyl, hydroxyphenyl-alkyl, and hydroxynaphthyl alkyl may contain 1–4 hydroxy substituents, and COE$_1$, stands for —C=O•E$_1$ Examples of —C=O•E$_1$ include, but are not limited to, acetyl and phenylpropionyl.

In this disclosure, the disulfide or amide bond which links two residues in a peptide of this invention are formed between the side-chain functionalities. This is, between the side-chain carboxyl group of an acidic amino acid residue (e.g., Asp, Glu, —NH((CH$_2$)$_3$COOH)CO—, or —NH((CH$_2$)$_4$COOH)CO—) and the side-chain amino group of a basic amino acid residue (e.g., Lys, Orn, —NHCH(CH$_2$NH$_2$)CO—, or —NHCH(CH$_2$)$_2$NH$_2$)CO—), or between the side-chain sulfhydryl groups of two Cys residues. In both formulas set forth herein, the amide or disulfide bond between two residues is not shown. A peptide of this invention is also denoted herein by another format, e.g., c[Lys$^{13}$,Asp$^{17}$][Nle$^{8,18}$,Tyr$^{34}$]bPTH(1-34)NH$_2$(SEQ ID NO:6), with the two linked residues placed between two brackets following "c" (e.g., Lys$^{13}$ and Asp$^{17}$), with substituted amino acids from the natural sequence placed between the second set of brackets (e.g., Nle$^8$ for Met$^{28}$, Nle$^{18}$ for Met$^{18}$, and Tyr$^{34}$ for Phe$^{34}$ in bPTH). The abbreviation bPTH stands for bovine PTH, rPTH for rat PTH, hPTH for human PTH, and hPTHrP for human PTHrP. The numbers between the parenthesis refer to the number of amino acids present in the peptide (e.g., the first 34 amino acids of bPTH).

In another embodiment, the side-chain functionalities of amino acid residues A$_{13}$ and A$_{17}$, A$_{26}$ and A$_{30}$, or A$_{13}$ and A$_{17}$ and A$_{26}$ and A$_{30}$ constitute a lanthionine bridge. Examples of lanthionine side-chain bridges are thioethers (e.g., —(CH$_2$)$_n$—S—(CH$_2$)$_m$— where m and n, independently, are 1–3) or dithioethers (e.g., —(CH$_2$)$_m$—S—(CH$_2$)$_n$—S—(CH$_2$)$_o$— where m, n, and o, independently, are 1–3. Examples of the synthesis of peptides containing lanthionines is described in Fukase, K., et al., Tetrahedron Let. 29:795–798 (1988); Labl, M., et al., Tetrahedron Let. 25:2067–2068 (1984); and Mosberg, H. I., Life Science 43:1013–1020 (1988).

The cyclic peptides of the invention can be used to stimulate the growth of bone in a subject (a mammal such as a human subject). Thus, the cyclic peptide are useful in the treatment of osteoporosis and bone fractures. The cyclic peptides of the invention can be administered concurrently with antiresorptive therapy, e.g., bisphosphonate and calcitonin.

The cyclic peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), polymeric acids (e.g., tannic acid, carboxymethyl cellulose, polylactic, polyglycolic, or copolymers of polylactic-glycolic acids).

A therapeutically effective amount of a cyclic peptide of this invention and a pharmaceutically acceptable carrier substance (e.g., magnesium carbonate, lactose, or a phospholipid with which the therapeutic compound can form a micelle) together form a therapeutic composition (e.g., a pill, tablet, capsule, or liquid) for administration (e.g., orally, intravenously, transdermally, pulmonarily, vaginally, subcutaneously, nasally, iontophoretically, or by intratracheally) to a subject in need of the peptide. The pill, tablet, or capsule can be coated with a substance capable of protecting the composition from the gastric acid or intestinal enzymes in the subject's stomach for a period of time sufficient to allow the composition to pass undigested into the subject's small intestine. The therapeutic composition can also be in the form of a biodegradable or nonbiodegradable sustained release formulation for subcutaneous or intramuscular administration. See, e.g., U.S. Pat. Nos. 3,773,919 and 4,767,628 and PCT application Ser. No. WO 94/00148. Continuous administration can also be obtained using an implantable or external pump (e.g., INFUSAID™ pump) to administer the therapeutic composition. The cyclic peptide can be administered intermittently, e.g., single daily injection, or continuously at a low dose, e.g., sustained release formulation.

The dose of a cyclic peptide of the present invention for treating the above-mentioned diseases or disorders varies depending upon the manner of administration, the age and the body weight of the subject, and the condition of the subject to be treated, and ultimately will be decided by the attending physician or veterinarian. Such an amount of the cyclic peptide as determined by the attending physician or veterinarian is referred to herein as a "therapeutically effective amount."

Also contemplated within the scope of this invention is a cyclic peptide covered by the above generic formulas for use in treating diseases or disorders associated with the need to stimulate bone growth, e.g., osteoporosis or fractures.

Other features and advantages of the present invention will be apparent from the detailed description and from the claims.

DESCRIPTION OF THE PREFERRED EMBODIMENTS

Synthesis

The peptides of the invention can be prepared by standard solid phase synthesis. See, e.g., Stewart, J. M., et al., Solid Phase Synthesis (Pierce Chemical Co., 2d ed. 1984). The following is a description of how Analog #1 was prepared. Other peptides of the invention can be prepared in an analogous manner by a person of ordinary skill in the art.

Analog I was synthesized on an APPLIED BIOSYSTEMS™ 430A Automated Peptide Synthesizer (Applied Biosystems Inc., Foster City, Calif.) using version 1.40 of the software for NMP/HOBt Boc based chemistry. The following side-chain protected amino acid derivatives obtained from Applied Biosystems, Inc. were used in the course of the synthesis: N-Boc-Arg($N^G$-Tosyl)-OH, N-Boc-Asp(cHex)-OH, N-Boc-Glu(OBzl)-OH, N-Boc-His(Bom)-OH, N-Boc-(2-Cl-Z)-OH, N-Boc-Ser(Bzl)-OH, N-Boc-Thr(Bzl)-OH. N-Boc-Asp(OFm)-OH and N-Boc-Lys(Fmoc)-OH were purchased from Bachem, Calif. (Torrance, Calif.). The synthesis was carried out a p-methylbenzhydrylamine HCl resin (0.57 meq N/g)(Applied Biosystems, Inc.) at a 0.5 mmol scale until residue $Arg^{21}$ when the synthesis was split and carried out at a 0.25 mmol scale until completion. All three Arg residues at positions 19–21 were double-coupled and then capped with $Ac_2O$.

The first four residues were coupled using the above automated synthesis. Extension of the fully protected resin-bound peptide N-Boc-Ile-His(Bom)-Thr(Bzl)-Ala-O-Resin was then carried out manually on a A5-6023 Variable-Rate Flask Shaker (St. John Assoc. Inc., Beltsville, Md.). Amino acid residues at positions 26–30 were manually incorporated, and the lactam ring was formed before reconvening the automated solid phase peptide synthesis. Each manual cycle included the following steps: 1) Dimethylchloride (DCM) wash (3×1 min); 2) Tetrahydorfuric acid (TFA) 50% in DCM (1×3 min, 1×20 min); 3) DCM wash (3×1 min); 4) Diisopropylethylamine (DIEA) 1.5% in DCM (2×1 min); 5) DIEA 1.5% in NMP (2×1 min); 6) DCM wash (3×1 min); 7) NMP wash (3×1 min); and 8) coupling: 2 mmol (4 eq.) of Boc-amino acid+2 mmol of HOBt in NMP+2 mmol of (diisopropylcarbodiimide) DIC and up to 13 ml of total volume with NMP. After 1 hour, 2 ml of dimethylsulfoxide (DMSO) were added. The reaction was checked with ninhydrin test. [Reaction times: Asp(OFm) 1.5 hrs.; Ala: 1.5 hrs.; Ile: 1.5 hrs.; Leu: 1.5 hrs.; Lys(FMOC): 2.5 hrs.; 9) NMP wash (3×1 min); and 10) DCM wash (3×1 min).

The cyclization was accomplished by coupling side chains in the following manner: 1) Deprotection with pipedrine 20% in NMP (1×3', 1×20 min); 2) DCM wash (3× 1 min); 3) NMP wash (3×1 min); 4) Coupling with benzotriazolyl-N-oxy-tris(dimethylamino)phosphonium hexafluorophosphate (BOP) 1.5 mmol (3 eq.) in dimethylformamide (DMF) (1 ml)+1.5% DIEA in NMP (12 ml) for 3 hours (negative ninhydrin test); 5) NMP wash (3×1 min); 6) DCM wash (3×1 min); 7) acetic anhydride 5% in NMP (1×10 min); 8) NMP wash (3×1 min); and 9) DCM wash (3×1 min).

The remaining 25 residues were coupled using the automated synthesis described above. The final side-chain protected peptidyl-resin (1.8 g.) was cleaved with HF/anisole (10% at −5° C. for 75 min). After removal of the HF under reduced pressure, the residue was washed consecutively with hexane and diethyl ether and filtered. The crude peptide was separated from the resin using 50% aqueous AcOH and the solution was lyophilized. The analytical HPLC profile of the crude peptide show a major peak ($t_R$=23.20 min.) corresponding to the product.

The crude peptide was purified with preparation HPLC on a VYDAC® protein C-18 reverse-phase column (5×30 cm) (Waters, Milford, Mass.) using the following solvent system: A=0.1% TFA in water and B=0.1% TFA in acetonitrile. The linear gradient used was: 0–10 min (0–10% B); and 10–200 min (10–50% B). The flow rate was 70 ml/min and fractions of 20 ml were collected and analyzed on an analytical HPLC. The pure fractions were pooled and lyophilized.

The full names for the abbreviations used above are as follows: Boc for 1-butyloxycarbonyl, OFm for O-formyl, OBzl is O-benzyl, BOM for benzyloxymethyl, Bzl for benzyl, $N^G$-Tosyl for tosyl at guanidyl site, HOBt for 1-hydroxybenzotriazole, NMP for N-methyl-2-pyrrolidone, Fmoc for 9-Fluoronylmethyloxycarbonyl, 2-Cl-Z for 2-chlorobenzyloxycarbonyl and O-cHex for O-cyclohexyl.

Other cyclic lactams of this invention can be prepared in an analogous manner by a person of ordinary skill in the art. Moreover, the disulfide bridge formation between the two Cys residues of a cyclic peptide of this invention can be achieved following general procedures described in the prior art. For example, see Coy, et al., U.S. Pat. No. 4,853,371; M. Bodanszky, et al., Chapter 6, Vol. 21, Chapter 6, Vol. 16, *The Practice of Peptide Synthesis* (Springer-Verlag, 1984).

PTH Receptor Binding

The cyclic peptide of the invention can be tested for the ability to bind to the PTH receptor present on SaOS-2 (human osteosarcoma cells). Saos-2 cells (American Type Culture Collection, Rockville, Md.; ATCC #HTB 85) are maintained in RPMI 1640 medium (Sigma, St. Louis, Mo.) supplemented with 10% fetal bovine serum (FBS) and 2 mM glutamine at 37° C. in a humidified atmosphere of 5% $CO_2$ in air. The medium is changed every three or four days, and the cells are subcultured every week by trypsinization.

Saos-2 cells are maintained for four days after they have reached confluence. The medium is replaced with 5% FBS in RPMI 1640 medium and incubated for 2 hrs at room temperature with $10 \times 10^4$ cpm mono-$^{125}$I-[$Nle^{8,18}$, $Tyr^{34}$ (3-$^{125}$I)]bPTH(1-34)$NH_2$ in the presence of a competing cyclic peptides of the invention, at various concentrations between $10^{-11}$ M to $10^{-4}$M. The cells are washed four times with ice-cold PBS and lysed with 0.1M NaOH, and the radioactivity associated with the cells is counted in a scintillation counter. Synthesis of mono-$^{125}$I-[Nle$^{8,18}$, Tyr$^{34}$(3-$^{125}$I)] bPTH(1-34)NH$_2$ is carried out as described in Goldman, M. E., et al., Endocrinology, 1988, 123, 1468–1475.

The binding assay was conducted with Analog I. The IC$_{50}$ (half maximal inhibition of binding of mono-$^{125}$I-[Nle$^{8,18}$, Tyr$^{34}$(3-$^{125}$I)]bPTH(1-34)NH$_2$) for Analog I was calculated to be 500 nM.

Stimulation of Adenylate Cyclase Release

The ability of the cyclic analogs of the invention to induce a biological response in SaOS-2 cells can also be measured. For example, the stimulation of the adenylate cyclase can be determined by measuring the level of synthesis of cAMP (adenosine 3':5'-cyclic monophosphate) as described previously in Rodan, et al., 1983, J. Clin. Invest. 72, 1511 and Goldman, et al., 1988, Endocrinology, 123, 1468. Confluent SaOS-2 cells in 24 wells plates are incubated with 0.5 μCi[$^3$H]adenine (26.9 Ci/mmol, New England Nuclear, Boston, Mass.) in fresh medium at 37° C. for 2 hrs, and washed twice with Hank's balanced salt solution (Gibco, Gaithersburg, Md.). The cells are treated with 1 mM IBMX [isobutylmethylxanthine, Sigma, St. Louis, Mo.] in fresh medium for 15 min, and the cyclic peptides are added to the medium to incubate for 5 min. The reaction is stopped by the addition of 1.2M trichloroacetic acid (TCA) (Sigma, St. Louis, Mo.) followed by sample neutralization with 4N KOH. cAMP is isolated by the two-column chromatographic method (Salmon, et al., 1974, Anal. Biochem. 58, 541). The radioactivity is counted in a scintillation counter (Liquid Scintillation Counter 2200CA, PACKARD, Downers Grove, Ill.).

The EC$_{50}$'s (half maximal stimulation of adenylate cyclase) for Analog I was calculated to be 20 nM. The cyclic peptide, thus, was a potent stimulator of adenylate cyclase activity in SaOS-2 cells. This biochemical pathway has been indicative as a proximal signal for osteoblast proliferation (e.g., bone growth).

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( C ) STRANDEDNESS: Not Relevant
        ( D ) TOPOLOGY: linear ( i i ) MOLECULE TYPE: protein ( i x ) FEATURE:
        ( D ) OTHER INFORMATION: The side chains of Lys at
        position 13 and Asp at postion 17 are linked by an
        amide bond, and this sequence has an amide C-terminus
        ( i . e . , CONH2 ), rather than a carboxy C-terminus
        ( i . e . , COOH ).

( x i ) SEQUENCE DESCRIPTION: SEQ ID NO:1:

```
Ser Val Ser Glu Ile Gln Leu Met His Asn Leu Gly Lys His Leu Asn
 1               5                  10                  15
Asp Met Glu Arg Val Glu Trp Leu Arg Lys Lys Leu Gln Asp Val His
                20                  25                  30
Asn Phe
```

( 2 ) INFORMATION FOR SEQ ID NO:2:

( i ) SEQUENCE CHARACTERISTICS:
        ( A ) LENGTH: 34 amino acids
        ( B ) TYPE: amino acid
        ( C ) STRANDEDNESS: Not Relevant
        ( D ) TOPOLOGY: linear ( i i ) MOLECULE TYPE: protein ( i x ) FEATURE:
        ( D ) OTHER INFORMATION: The side chains of Lys at
        position 13 and Asp at postion 17 are linked by an amide bond, and this sequence has an amide C-terminus
(i.e., CONH2), rather than a carboxy C-terminus
(i.e., COOH).

(x i) SEQUENCE DESCRIPTION: SEQ ID NO:2:

Ala Val Ser Glu Ile Gln Phe Met His Asn Leu Gly Lys His Leu Asp
1               5                   10                  15

Ser Met Glu Arg Val Glu Trp Leu Arg Lys Lys Leu Gln Asp Val His
                20                  25                  30

Asn Phe (2) INFORMATION FOR SEQ ID NO:3:

(i) SEQUENCE CHARACTERISTICS:
      (A) LENGTH: 34 amino acids
      (B) TYPE: amino acid
      (C) STRANDEDNESS: Not Relevant
      (D) TOPOLOGY: linear (i i) MOLECULE TYPE: protein (i x) FEATURE:
      (D) OTHER INFORMATION: The side chains of Lys at
         position 13 and Asp at postion 17 are linked by an
         amide bond, and this sequence has an amide C-terminus
         (i.e., CONH2), rather than a carboxy C-terminus
         (i.e., COOH).

(x i) SEQUENCE DESCRIPTION: SEQ ID NO:3:

Ala Val Ser Glu Ile Gln Leu Met His Asn Leu Gly Lys His Leu Ala
1               5                   10                  15

Asp Val Glu Arg Met Gln Trp Leu Arg Lys Lys Leu Gln Asp Val His
                20                  25                  30

Asn Phe (2) INFORMATION FOR SEQ ID NO:4:

(i) SEQUENCE CHARACTERISTICS:
      (A) LENGTH: 34 amino acids
      (B) TYPE: amino acid
      (C) STRANDEDNESS: Not Relevant
      (D) TOPOLOGY: linear (i i) MOLECULE TYPE: protein (i x) FEATURE:
      (D) OTHER INFORMATION: The side chains of Lys at
         position 13 and Asp at postion 17 are linked by an
         amide bond, and this sequence has an amide C-terminus
         (i.e., CONH2), rather than a carboxy C-terminus
         (i.e., COOH).

(i x) FEATURE:
      (D) OTHER INFORMATION: Xaa at postions 8 and 18
         are Norleucine.

(x i) SEQUENCE DESCRIPTION: SEQ ID NO:4:

Ser Val Ser Glu Ile Gln Leu Xaa His Asn Leu Gly Lys His Leu Asn
1               5                   10                  15

Asp Xaa Glu Arg Val Glu Trp Leu Arg Lys Lys Leu Gln Asp Val His
                20                  25                  30

Asn Tyr (2) INFORMATION FOR SEQ ID NO:5:

(i) SEQUENCE CHARACTERISTICS:
      (A) LENGTH: 34 amino acids
      (B) TYPE: amino acid (C) STRANDEDNESS: Not Relevant
(D) TOPOLOGY: linear (i i) MOLECULE TYPE: protein (i x) FEATURE:
(D) OTHER INFORMATION: The side chains of Lys at position 13 and Asp at postion 17 are linked by an amide bond, and this sequence has an amide C-terminus (i.e., CONH2), rather than a carboxy C-terminus (i.e., COOH).

(i x) FEATURE:
(D) OTHER INFORMATION: Xaa at postions 8 and 18 are Norleucine.

(x i) SEQUENCE DESCRIPTION: SEQ ID NO:5:

| Ala | Val | Ser | Glu | Ile | Gln | Leu | Xaa | His | Asn | Leu | Gly | Lys | His | Leu | Ala |
|---|---|---|---|---|---|---|---|---|---|---|---|---|---|---|---|
| 1 | | | | 5 | | | | | 10 | | | | | 15 | |

| Asp | Xaa | Glu | Arg | Met | Gln | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

Asn Tyr (2) INFORMATION FOR SEQ ID NO:6:

(i) SEQUENCE CHARACTERISTICS:
(A) LENGTH: 34 amino acids
(B) TYPE: amino acid
(C) STRANDEDNESS: Not Relevant
(D) TOPOLOGY: linear (i i) MOLECULE TYPE: protein (i x) FEATURE:
(D) OTHER INFORMATION: The side chains of Lys at position 13 and Asp at postion 17 are linked by an amide bond, and this sequence has an amide C-terminus (i.e., CONH2), rather than a carboxy C-terminus (i.e., COOH).

(i x) FEATURE:
(D) OTHER INFORMATION: Xaa at postions 8 and 18 are Norleucine.

(x i) SEQUENCE DESCRIPTION: SEQ ID NO:6:

| Ala | Val | Ser | Glu | Ile | Gln | Phe | Xaa | His | Asn | Leu | Gly | Lys | His | Leu | Ser |
|---|---|---|---|---|---|---|---|---|---|---|---|---|---|---|---|
| 1 | | | | 5 | | | | | 10 | | | | | 15 | |

| Asp | Xaa | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

Asn Tyr (2) INFORMATION FOR SEQ ID NO:7:

(i) SEQUENCE CHARACTERISTICS:
(A) LENGTH: 34 amino acids
(B) TYPE: amino acid
(C) STRANDEDNESS: Not Relevant
(D) TOPOLOGY: linear (i i) MOLECULE TYPE: protein (i x) FEATURE:
(D) OTHER INFORMATION: The side chains of Lys at position 26 and Asp at position 30 are linked by an amide bond, and this sequence has an amide C-terminus (i.e., CONH2), rather than a carboxy C-terminus (i.e., COOH).

(x i) SEQUENCE DESCRIPTION: SEQ ID NO:7:

| Ser | Val | Ser | Glu | Ile | Gln | Leu | Met | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

Ser Met Glu Arg Val Glu Trp Leu Arg Lys Lys Leu Gln Asp Val His
        20                  25                  30
Asn Phe ( 2 ) INFORMATION FOR SEQ ID NO:8:

( i ) SEQUENCE CHARACTERISTICS:
        ( A ) LENGTH: 34 amino acids
        ( B ) TYPE: amino acid
        ( C ) STRANDEDNESS: Not Relevant
        ( D ) TOPOLOGY: linear ( i i ) MOLECULE TYPE: protein ( i x ) FEATURE:
        ( D ) OTHER INFORMATION: The side chains of Lys at
            position 26 and Asp at position 30 are linked by an
            amide bond, and this sequence has an amide C-terminus
            ( i . e . ,    C O N H 2 ), rather than a carboxy C-terminus
            ( i . e . ,    C O O H ).

( x i ) SEQUENCE DESCRIPTION: SEQ ID NO:8:

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
        20                  25                  30

Asn Phe ( 2 ) INFORMATION FOR SEQ ID NO:9:

( i ) SEQUENCE CHARACTERISTICS:
        ( A ) LENGTH: 34 amino acids
        ( B ) TYPE: amino acid
        ( C ) STRANDEDNESS: Not Relevant
        ( D ) TOPOLOGY: linear ( i i ) MOLECULE TYPE: protein ( i x ) FEATURE:
        ( D ) OTHER INFORMATION: The side chains of Lys at
            position 26 and Asp at position 30 are linked by an
            amide bond, and this sequence has an amide C-terminus
            ( i . e . ,    C O N H 2 ), rather than a carboxy C-terminus
            ( i . e . ,    C O O H ).

( x i ) SEQUENCE DESCRIPTION: SEQ ID NO:9:

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
        20                  25                  30

Asn Phe ( 2 ) INFORMATION FOR SEQ ID NO:10:

( i ) SEQUENCE CHARACTERISTICS:
        ( A ) LENGTH: 34 amino acids
        ( B ) TYPE: amino acid
        ( C ) STRANDEDNESS: Not Relevant
        ( D ) TOPOLOGY: linear ( i i ) MOLECULE TYPE: protein ( i x ) FEATURE:
        ( D ) OTHER INFORMATION: The side chains of Lys at
            position 26 and Asp at position 30 are linked by an
            amide bond, and this sequence has an amide C-terminus
            ( i . e . ,    C O N H 2 ), rather than a carboxy C-terminus
            ( i . e . ,    C O O H ).

( i x ) FEATURE:
 ( D ) OTHER INFORMATION: Xaa at postions 8 and 18
  are Norleucine.

( x i ) SEQUENCE DESCRIPTION: SEQ ID NO:10:

Ser Val Ser Glu Ile Gln Leu Xaa His Asn Leu Gly Lys His Leu Asn
1               5                   10                  15

Ser Xaa Glu Arg Val Glu Trp Leu Arg Lys Lys Leu Gln Asp Val His
            20                  25                  30

Asn Tyr ( 2 ) INFORMATION FOR SEQ ID NO:11:

( i ) SEQUENCE CHARACTERISTICS:
  ( A ) LENGTH: 34 amino acids
  ( B ) TYPE: amino acid
  ( C ) STRANDEDNESS: Not Relevant
  ( D ) TOPOLOGY: linear ( i i ) MOLECULE TYPE: protein ( i x ) FEATURE:
  ( D ) OTHER INFORMATION: The side chains of Lys at
   position 26 and Asp at position 30 are linked by an
   amide bond, and this sequence has an amide C-terminus
   ( i . e . , CONH2 ), rather than a carboxy C-terminus
   ( i . e . , COOH ).

( i x ) FEATURE:
  ( D ) OTHER INFORMATION: Xaa at postions 8 and 18
   are Norleucine.

( x i ) SEQUENCE DESCRIPTION: SEQ ID NO:11:

Ala Val Ser Glu Ile Gln Phe Xaa His Asn Leu Gly Lys His Leu Ser
1               5                   10                  15

Ser Xaa Glu Arg Val Glu Trp Leu Arg Lys Lys Leu Gln Asp Val His
            20                  25                  30

Asn Tyr ( 2 ) INFORMATION FOR SEQ ID NO:12:

( i ) SEQUENCE CHARACTERISTICS:
  ( A ) LENGTH: 34 amino acids
  ( B ) TYPE: amino acid
  ( C ) STRANDEDNESS: Not Relevant
  ( D ) TOPOLOGY: linear ( i i ) MOLECULE TYPE: protein ( i x ) FEATURE:
  ( D ) OTHER INFORMATION: The side chains of Lys at
   position 26 and Asp at position 30 are linked by an
   amide bond, and this sequence has an amide C-terminus
   ( i . e . , CONH2 ), rather than a carboxy C-terminus
   ( i . e . , COOH ).

( i x ) FEATURE:
  ( D ) OTHER INFORMATION: Xaa at postions 8 and 18
   are Norleucine.

( x i ) SEQUENCE DESCRIPTION: SEQ ID NO:12:

Ala Val Ser Glu Ile Gln Leu Xaa His Asn Leu Gly Lys His Leu Ala
1               5                   10                  15

Ser Xaa Glu Arg Met Gln Trp Leu Arg Lys Lys Leu Gln Asp Val His
            20                  25                  30

Asn Tyr ( 2 ) INFORMATION FOR SEQ ID NO:13:

( i ) SEQUENCE CHARACTERISTICS:
  ( A ) LENGTH: 34 amino acids
  ( B ) TYPE: amino acid
  ( C ) STRANDEDNESS: Not Relevant
  ( D ) TOPOLOGY: linear ( i i ) MOLECULE TYPE: protein ( i x ) FEATURE:
  ( D ) OTHER INFORMATION: The side chains of Lys at
    position 13 and Asp at position 17 and the side chains
    of Lys at position 26 and Asp at position 30 are linked
    byy an amide bond, and this sequence has an amide
    C-terminus (i.e., COOH).

( x i ) SEQUENCE DESCRIPTION: SEQ ID NO:13:

| Ser | Val | Ser | Glu | Ile | Gln | Leu | Met | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Asp | Met | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

Asn Phe ( 2 ) INFORMATION FOR SEQ ID NO:14:

( i ) SEQUENCE CHARACTERISTICS:
  ( A ) LENGTH: 34 amino acids
  ( B ) TYPE: amino acid
  ( C ) STRANDEDNESS: Not Relevant
  ( D ) TOPOLOGY: linear ( i i ) MOLECULE TYPE: protein ( i x ) FEATURE:
  ( D ) OTHER INFORMATION: The side chains of Lys at
    position 13 and Asp at position 17 and the side chains
    of Lys at position 26 and Asp at position 30 are linked
    byy an amide bond, and this sequence has an amide
    C-terminus (i.e., COOH).

( x i ) SEQUENCE DESCRIPTION: SEQ ID NO:14:

| Ala | Val | Ser | Glu | Ile | Gln | Phe | Met | His | Asn | Leu | Gly | Lys | His | Leu | Ser |
|---|---|---|---|---|---|---|---|---|---|---|---|---|---|---|---|
| 1 | | | | 5 | | | | | 10 | | | | | 15 | |

| Asp | Met | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

Asn Phe ( 2 ) INFORMATION FOR SEQ ID NO:15:

( i ) SEQUENCE CHARACTERISTICS:
  ( A ) LENGTH: 34 amino acids
  ( B ) TYPE: amino acid
  ( C ) STRANDEDNESS: Not Relevant
  ( D ) TOPOLOGY: linear ( i i ) MOLECULE TYPE: protein ( i x ) FEATURE:
  ( D ) OTHER INFORMATION: The side chains of Lys at
    position 13 and Asp at position 17 and the side chains
    of Lys at position 26 and Asp at position 30 are linked
    byy an amide bond, and this sequence has an amide
    C-terminus (i.e., COOH).

( x i ) SEQUENCE DESCRIPTION: SEQ ID NO:15:

| Ala | Val | Ser | Glu | Ile | Gln | Leu | Met | His | Asn | Leu | Gly | Lys | His | Leu | Ala |
|---|---|---|---|---|---|---|---|---|---|---|---|---|---|---|---|
| 1 | | | | 5 | | | | | 10 | | | | | 15 | |

| Asp | Val | Glu | Arg | Met | Gln | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

Asn Phe (2) INFORMATION FOR SEQ ID NO:16:

(i) SEQUENCE CHARACTERISTICS:
        (A) LENGTH: 34 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: The side chains of Lys at
        position 13 and Asp at position 17 and the side chains
        of Lys at position 26 and Asp at position 30 are linked
        byy an amide bond, and this sequence has an amide
        C-terminus (i.e., COOH).

(ix) FEATURE:
        (D) OTHER INFORMATION: Xaa at postions 8 and 18
        are Norleucine.

(xi) SEQUENCE DESCRIPTION: SEQ ID NO:16:

```
Ser Val Ser Glu Ile Gln Leu Xaa His Asn Leu Gly Lys His Leu Asn
1               5                   10                  15
Asp Xaa Glu Arg Val Glu Trp Leu Arg Lys Lys Leu Gln Asp Val His
            20                  25                  30
Asn Tyr
```

(2) INFORMATION FOR SEQ ID NO:17:

(i) SEQUENCE CHARACTERISTICS:
        (A) LENGTH: 34 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: The side chains of Lys at
        position 13 and Asp at position 17 and the side chains
        of Lys at position 26 and Asp at position 30 are linked
        byy an amide bond, and this sequence has an amide
        C-terminus (i.e., COOH).

(ix) FEATURE:
        (D) OTHER INFORMATION: Xaa at postions 8 and 18
        are Norleucine.

(xi) SEQUENCE DESCRIPTION: SEQ ID NO:17:

```
Ala Val Ser Glu Ile Gln Leu Xaa His Asn Leu Gly Lys His Leu Ala
1               5                   10                  15
Asp Xaa Glu Arg Met Gln Trp Leu Arg Lys Lys Leu Gln Asp Val His
            20                  25                  30
Asn Tyr
```

(2) INFORMATION FOR SEQ ID NO:18:

(i) SEQUENCE CHARACTERISTICS:
        (A) LENGTH: 34 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: The side chains of Lys at
        position 13 and Asp at position 17 and the side chains of Lys at position 26 and Asp at position 30 are linked
byy an amide bond, and this sequence has an amide
C-terminus (i.e., COOH).

( i x ) FEATURE:
( D ) OTHER INFORMATION: Xaa at postions 8 and 18
are Norleucine.

( x i ) SEQUENCE DESCRIPTION: SEQ ID NO:18:

Ala Val Ser Glu Ile Gln Phe Xaa His Asn Leu Gly Lys His Leu Ser
1               5                   10                  15

Asp Xaa Glu Arg Val Glu Trp Leu Arg Lys Lys Leu Gln Asp Val His
                20                  25                  30

Asn Tyr ( 2 ) INFORMATION FOR SEQ ID NO:19:

( i ) SEQUENCE CHARACTERISTICS:
( A ) LENGTH: 34 amino acids
( B ) TYPE: amino acid
( C ) STRANDEDNESS: Not Relevant
( D ) TOPOLOGY: linear ( i i ) MOLECULE TYPE: protein ( i x ) FEATURE:
( D ) OTHER INFORMATION: Xaa in position 13 is A13,
Xaa in position 17 is A17, Xaa in position 22 is A22,
Xaa in position25 is A25, Xaa in position 26 is A26, Xaa
in position 29 is A29, Xaa in position 30 is A30, Xaa in
position 31 is A31, Xaa in position 32 is A32, Xaa in
position 33 is A33, Xaa in position 34 is A34.

( x i ) SEQUENCE DESCRIPTION: SEQ ID NO:19:

Ala Val Ser Gln His Gln Leu Leu His Asp Lys Gly Xaa Ser Ile Gln
1               5                   10                  15

Xaa Leu Arg Arg Arg Xaa Phe Leu Xaa Xaa Leu Ile Xaa Xaa Xaa Xaa
                20                  25                  30

Xaa Xaa ( 2 ) INFORMATION FOR SEQ ID NO:20:

( i ) SEQUENCE CHARACTERISTICS:
( A ) LENGTH: 34 amino acids
( B ) TYPE: amino acid
( C ) STRANDEDNESS: Not Relevant
( D ) TOPOLOGY: linear ( i i ) MOLECULE TYPE: protein ( i x ) FEATURE:
( D ) OTHER INFORMATION: The side chains of Lys at
position 13 and Asp at postion 17 are linked by an amide
bond, and this sequence has an amide C-terminus (i.e.,
CONH2), rather than a carboxy C-terminus (i.e., COOH).

( x i ) SEQUENCE DESCRIPTION: SEQ ID NO:20:

Ala Val Ser Glu His Gln Leu Leu His Asp Lys Gly Lys Ser Ile Gln
1               5                   10                  15

Asp Leu Arg Arg Arg Phe Phe Leu His Leu Leu Ile Ala Glu Ile His
                20                  25                  30

Thr Ala ( 2 ) INFORMATION FOR SEQ ID NO:21:

( i ) SEQUENCE CHARACTERISTICS:
( A ) LENGTH: 34 amino acids
( B ) TYPE: amino acid (C) STRANDEDNESS: Not Relevant
(D) TOPOLOGY: linear (i i) MOLECULE TYPE: protein (i x) FEATURE:
(D) OTHER INFORMATION: The side chains of Lys at
position 26 and Asp at position 30 are linked by an
amide bond, and this sequence has an amide C-terminus
(i. e., CONH2), rather than a carboxy C-terminus (i.e.,
COOH).

(x i) SEQUENCE DESCRIPTION: SEQ ID NO:21:

Ala Val Ser Glu His Gln Leu Leu His Asp Lys Gly Lys Ser Ile Gln
1               5                   10                  15

Asp Leu Arg Arg Arg Phe Phe Leu His Lys Leu Ile Ala Asp Ile His
            20                  25                  30

Thr Ala (2) INFORMATION FOR SEQ ID NO:22:

(i) SEQUENCE CHARACTERISTICS:
    (A) LENGTH: 34 amino acids
    (B) TYPE: amino acid
    (C) STRANDEDNESS: Not Relevant
    (D) TOPOLOGY: linear (i i) MOLECULE TYPE: protein (i x) FEATURE:
(D) OTHER INFORMATION: The side chains of Lys at
position 13 and Asp at position 17 and the side chains
of Lys at position 26 and Asp at position 30 are linked
byy an amide bond, and this sequence has an amide
C-terminus (i.e., COOH).

(x i) SEQUENCE DESCRIPTION: SEQ ID NO:22:

Ala Val Ser Glu His Gln Leu Leu His Asp Lys Gly Lys Ser Ile Gln
1               5                   10                  15

Asp Leu Arg Arg Arg Phe Phe Leu His Lys Leu Ile Ala Asp Ile His
            20                  25                  30

Thr Ala

---

What is claimed is:
1. A cyclic polypeptide of the formula:

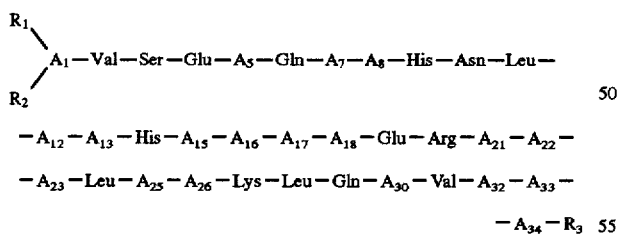

wherein:
$A_1$ is Ser or Ala;
$A_5$ is Ile or Met;
$A_7$ is Leu or Phe;
$A_8$ is Met, Nle, or Val;
$A_{12}$ is Gly, Glu, Aib, Ala, or D-Ala;
$A_{13}$ is the D- or L- isomer selected from the group consisting of Cys, Hcy, Lys, Orn, NHCH(CH$_2$NH$_2$)CO, NHCH((CH$_2$)$_2$NH$_2$)CO, Asp, Glu, NHCH((CH$_2$)$_3$COOH)CO, and NHCH((CH$_2$)$_4$COOH)CO;
$A_{15}$ is Leu or Arg;
$A_{16}$ is Ser, His, Asn, or Ala;
$A_{17}$ is the D- or L- isomer selected from the group consisting of Ser, Thr, Cys, Hcy, Lys, Orn, NHCH(CH$_2$NH$_2$)CO, NHCH((CH$_2$)$_2$NH$_2$)CO, Asp, Glu, NHCH((CH$_2$)$_3$COOH)CO, and NHCH((CH$_2$)$_4$COOH)CO;
$A_{18}$ is Met, Leu, Nle, or Val;
$A_{21}$ is Met, Leu, Nle, Gln, or Val;
$A_{22}$ is Glu, Asp, or Gln;
$A_{23}$ is Trp, 1-Nal, or 2-Nal;
$A_{25}$ is Arg or Gln;
$A_{26}$ is the D- or L- isomer selected from the group consisting of Cys, Hcy, Lys, Orn, NHCH(CH$_2$NH$_2$)CO, NHCH((CH$_2$)$_2$NH$_2$)CO, Asp, Glu, NHCH((CH$_2$)$_3$COOH)CO, and NHCH((CH$_2$)$_4$COOH)CO;
$A_{30}$ is the D- or L- isomer selected from the group consisting of Cys, Hcy, Lys, Orn, NH—CH(CH$_2$NH$_2$)CO, NHCH((CH$_2$)$_2$NH$_2$)CO, Asp, Glu, NHCH((CH$_2$)$_3$COOH)CO, and NHCH((CH$_2$)$_4$COOH)CO;
$A_{32}$ is His or is deleted;
$A_{33}$ is Asn, Ser, or is deleted;
$A_{34}$ is Ala, Phe, Tyr, p-X-Phe (where X is a halogen or CH$_3$), or is deleted;

25 each $R_1$ and $R_2$ is, independently, H, $C_{1-12}$ alkyl, $C_{7-20}$ phenylalkyl, $C_{11-20}$ napthylalkyl, $C_{1-12}$ hydroxyalkyl, $C_{7-20}$ hydroxyphenyl, $C_{11-20}$ hydroxynapthylalkyl, $COE_1$ where $E_1$ is $C_{1-20}$ alkyl, $C_{7-20}$ phenylalkyl, $C_{11-20}$ napthylalkyl, $C_{1-12}$ hydroxyalkyl, $C_{7-20}$ hydroxyphenylalkyl, $C_{11-20}$ hydroxynapthylalkyl, $C_{3-20}$ alkenyl, $C_{3-20}$ alkenyl, $C_{3-20}$ alkynyl, phenyl, napthyl, $C_{7-10}$ phenylalkyl, or $C_{1-12}$ acyl;

$R_3$ is OH, $NH_2$, $C_{1-12}$ alkoxy, $C_{7-10}$ phenylalkoxy, $C_{8-20}$ napthylalkoxy, NH—Y—$CH_2$—Z where Y is a $C_{1-12}$ hydrocarbon moiety and Z is H, OH, $CO_2H$ or $CONH_2$, or $NR_1R_2$; and a disulfide or amide bond links the side chains of residues $A_{13}$ and $A_{17}$, $A_{26}$ and $A_{30}$, or $A_{13}$ and $A_{17}$ and $A_{26}$ and $A_{30}$.

2. A cyclic polypeptide of claim 1, wherein $A_5$ is Ile; $A_7$ is Phe or Leu; $A_8$ is Met or Nle; $A_{12}$ is Gly; $A_{15}$ is Leu; $A_{16}$ is Ser, Asn, or Ala; $A_{18}$ is Met, Val, or Nle; $A_{21}$ is Met or Val; $A_{22}$ is Glu or Gln; $A_{23}$ is Trp; $A_{25}$ is Arg; $A_{32}$ is His; $A_{33}$ is Asn; and $A_{34}$ is Phe or Try.

3. A cyclic polypeptide of claim 2, wherein $A_{13}$ is Lys; $A_{17}$ is Asp; $A_{26}$ is Lys; $A_{30}$ is Asp; and an amide bond links the side chains of $A_{13}$ and $A_{17}$; or a pharmaceutically acceptable salt thereof.

4. A cyclic polypeptide of claim 3, wherein said cyclic polypeptide is c[$Lys^{13}$, $Asp^{17}$]hPTH(1-34)$NH_2$(SEQ ID NO:1); c[$Lys^{13}$, $Asp^{17}$]bPTH(1-34)$NH_2$(SEQ ID NO:2); c[$Lys^{13}$, $Asp^{17}$]rPTH(1-34)$NH_2$(SEQ ID NO:3); c[$Lys^{13}$, $Asp^{17}$][$Nle^{8,18}$, $Tyr^{34}$]hPTH(1-34)$NH_2$(SEQ ID NO:4); c[$Lys^{13}$, $Asp^{17}$][$Nle^{8,18}$, $Tyr^{34}$]rPTH(1-34)$NH_2$(SEQ ID NO:5); or c[$Lys^{13}$, $Asp^{17}$][$Nle^{8,18}$, $Tyr^{34}$]bPTH(1-34)$NH_2$ (SEQ ID NO:6); or a pharmaceutically acceptable salt thereof.

5. A cyclic polypeptide of claim 2, wherein $A_{13}$ is Lys; $A_{17}$ is Asp; $A_{26}$ is Lys; $A_{30}$ is Asp; and an amide bond links the side chains of $A_{26}$ and $A_{30}$; or a pharmaceutically acceptable salt thereof.

6. A cyclic polypeptide of claim 5, wherein said cyclic polypeptide is c[$Lys^{26}$, $Asp^{30}$]hPTH(1-34)$NH_2$(SEQ ID NO:7); c[$Lys^{26}$, $Asp^{30}$]bPTH(1-34)$NH_2$(SEQ ID NO:8); c[$Lys^{26}$, $Asp^{30}$]rPTH(1-34)$NH_2$(SEQ ID NO:9); c[$Lys^{26}$, $Asp^{30}$][$Nle^{8,18}$, $Tyr^{34}$]hPTH(1-34)$NH_2$(SEQ ID NO:10); c[$Lys^{26}$, $Asp^{30}$][$Nle^{8,18}$, $Tyr^{34}$]bPTH(1-34)$NH_2$(SEQ ID NO:11); or c[$Lys^{26}$, $Asp^{30}$][$Nle^{8,18}$, $Tyr^{34}$]rPTH(1-34) $NH_2$ (SEQ ID NO:12); or a pharmaceutically acceptable salt thereof.

7. A cyclic polypeptide of claim 2, wherein $A_{13}$ is Lys; $A_{17}$ is Asp; $A_{26}$ is Lys; $A_{30}$ is Asp; and a first amide bond links the side chains of $A_{13}$ and $A_{17}$ and a second amide bond links the side chains of $A_{26}$ and $A_{30}$; or a pharmaceutically acceptable salt thereof.

8. A cyclic polypeptide of claim 3, wherein said cyclic polypeptide is c[$Lys^{13}$, $Asp^{17}$]c[$Lys^{26}$, $Asp^{30}$]hPTH(1-34)$NH_2$(SEQ ID NO:13); c[$Lys^{13}$, $Asp^{17}$]c[$Lys^{26}$, $Asp^{30}$]bPTH (1-34)$NH_2$(SEQ ID NO:14); c[$Lys^{13}$, $Asp^{17}$]c[$Lys^{26}$, $Asp^{30}$]rPTH(1-34)$NH_2$(SEQ ID NO:15); c[$Lys^{13}$, $Asp^{17}$]c[$Lys^{26}$, $Asp^{30}$][$Nle^{8,18}$, $Tyr^{34}$] hPTH(1-34)$NH_2$(SEQ ID NO:16); c[$Lys^{13}$, $Asp^{17}$]c[$Lys^{26}$, $Asp^{30}$][$Nle^{8,18}$, $Tyr^{34}$]rPTH (1-34) $NH_2$(SEQ ID NO:17); or c[$Lys^{13}$, $Asp^{17}$]c[$Lys^{26}$, $Asp^{30}$] [$Nle^{8,18}$, $Tyr^{34}$]bPTH(1-34)$NH_2$(SEQ ID NO:18); or a pharmaceutically acceptable salt thereof.

26

9. A cyclic polypeptide of the formula:

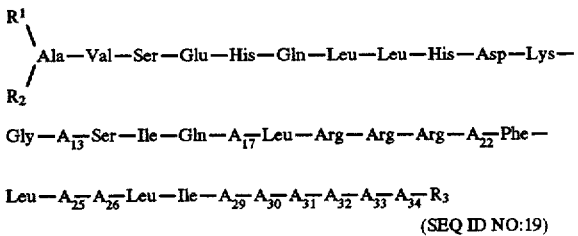

(SEQ ID NO:19)

wherein:

$A_{13}$ is the D- or L- isomer selected from the group consisting of Cys, Hcy, Lys, Orn, $NHCH(CH_2NH_2)CO$, $NHCH((CH_2)_2NH_2)CO$, Asp, Glu, $NHCH((CH_2)_3COOH)CO$, and $NHCH((CH_2)_4COOH)CO$;

$A_{17}$ is the D- or L- isomer selected from the group consisting of Cys, Hcy, Lys, Orn, $NHCH(CH_2NH_2)CO$, $NHCH((CH_2)_2NH_2)CO$, Asp, Glu, $NHCH((CH_2)_3COOH)CO$, and $NHCH((CH_2)_4COOH)CO$;

$A_{22}$ is Phe or Ile;

$A_{25}$ is His or Gln;

$A_{26}$ is the D- or L- isomer selected from the group consisting of Cys, Hcy, Lys, Orn, $NHCH(CH_2NH_2)CO$, $NHCH((CH_2)_2NH_2)CO$, Asp, Glu, $NHCH((CH_2)_3COOH)CO$, and $NHCH((CH_2)_4COOH)CO$;

$A_{29}$ is Ala or Glu;

$A_{30}$ is the D- or L- isomer selected from the group consisting of Glu, Cys, Hcy, Lys, Orn, $NHCH(CH_2NH_2)CO$, $NHCH((CH_2)_2NH_2)CO$, Asp, Glu, $NHCH((CH_2)_3COOH)CO$, $NHCH((CH_2)_4COOH)CO$, and [-$(CH_2)_n$-S-$(CH_2)_m$-];

$A_{31}$ is Ile or Val; and $A_{32}$ is His, Asn, or is deleted;

$A_{33}$ is Thr or is deleted;

$A_{34}$ is Ala or is deleted;

each $R_1$ and $R_2$ is, independently, H, $C_{1-12}$ alkyl, $C_{7-20}$ phenylalkyl, $C_{11-20}$ napthylalkyl, $C_{1-12}$ hydroxyalkyl, $C_{7-20}$ hydroxyphenyl, $C_{11-20}$ hydroxynapthylalkyl, $COE_1$ where $E_1$ is $C_{1-20}$ alkyl, $C_{3-20}$ alkenyl, $C_{3-20}$ alkynyl, phenyl, napthyl, $C_{7-20}$ phenylalkyl, $C_{11-20}$ napthylalkyl, $C_{1-12}$ hydroxyalkyl, $C_{7-20}$ hydroxyphenylalkyl, $C_{11-20}$ hydroxynapthylalkyl, or $C_{1-12}$ acyl;

$R_3$ is OH, $C_{1-12}$ alkoxy, $C_{7-10}$ phenylalkoxy, $C_{8-20}$ napthylalkoxy, NH—Y—$CH_2$—Z where Y is a $C_{1-12}$ hydrocarbon moiety and Z is H, OH, $CO_2H$ or $CONH_2$, or $NR_1R_2$; and a disulfide or amide bond links the side chains of residues $A_{13}$ and $A_{17}$, $A_{26}$ and $A_{30}$, or $A_{13}$ and $A_{17}$ and $A_{26}$ and $A_{30}$.

10. A cyclic polypeptide of claim 9, wherein $A_{22}$ is Phe; $A_{25}$ is His; $A_{29}$ is Ala; $A_{31}$ is Ile; $A_{32}$ is His; $A_{33}$ is Thr; and $A_{34}$ is Ala.

11. A cyclic polypeptide of claim 10, wherein $A_{13}$ is Lys; $A_{17}$ is Asp; $A_{26}$ is Lys; $A_{30}$ is Asp; and an amide bond links the side chains of $A_{13}$ and $A_{17}$; or a pharmaceutically acceptable salt thereof.

12. A cyclic polypeptide of claim 11, wherein said cyclic polypeptide is c[$Lys^{13}$, $Asp^{17}$]hPTHrP(1-34)$NH_2$(SEQ ID NO:20) or a pharmaceutically acceptable salt thereof.

13. A cyclic polypeptide of claim 10, wherein $A_{13}$ is Lys; $A_{17}$ is Asp; $A_{26}$ is Lys; $A_{30}$ is Asp; and an amide bond links the side chains of $A_{26}$ and $A_{30}$; or a pharmaceutically acceptable salt thereof.

14. A cyclic polypeptide of claim 13, wherein said cyclic polypeptide agonist is c[Lys$^{26}$, Asp$^{30}$]hPTHrP(1-34)NH$_2$ (SEQ ID NO:21) or a pharmaceutically acceptable salt thereof.

15. A cyclic polypeptide of claim 10, wherein $A_{13}$ is Lys; $A_{17}$ is Asp; $A_{26}$ is Lys; $A_{30}$ is Asp; and an amide bond links the side chains of $A_{13}$ and $A_{17}$ and $A_{26}$ and $A_{30}$; or a pharmaceutically acceptable salt thereof.

16. A cyclic polypeptide of claim 15, wherein said cyclic polypeptide is c[Lys$^{13}$, Asp$^{17}$]c[Lys$^{26}$, Asp$^{30}$]hPTHrP(1-34)NH$_2$(SEQ ID NO:22) or a pharmaceutically acceptable salt thereof.

* * * * *